US00PP32789P2

(12) United States Plant Patent
Smit

(10) Patent No.: US PP32,789 P2
(45) Date of Patent: Feb. 2, 2021

(54) ***BEGONIA* PLANT NAMED 'EC-BEGO-1902'**

(50) Latin Name: *Begonia masoniana*
Varietal Denomination: EC-BEGO-1902

(71) Applicant: Eden Collection BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 16/873,177

(22) Filed: Feb. 18, 2020

(51) Int. Cl.
*A01H 5/02* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Begonia masoniana* plant named 'EC-BEGO-1902' is disclosed, characterized by large leaves with long, thick petioles. Foliage is uniquely colored with a striking brown leaf rim against bright green leaves and distinct brown palmate center patch along veins. Upper leaf surfaces are puckered and hairy. The new variety is a *Begonia*, and is normally used as an ornamental garden or container plant.

2 Drawing Sheets

Figure 1:
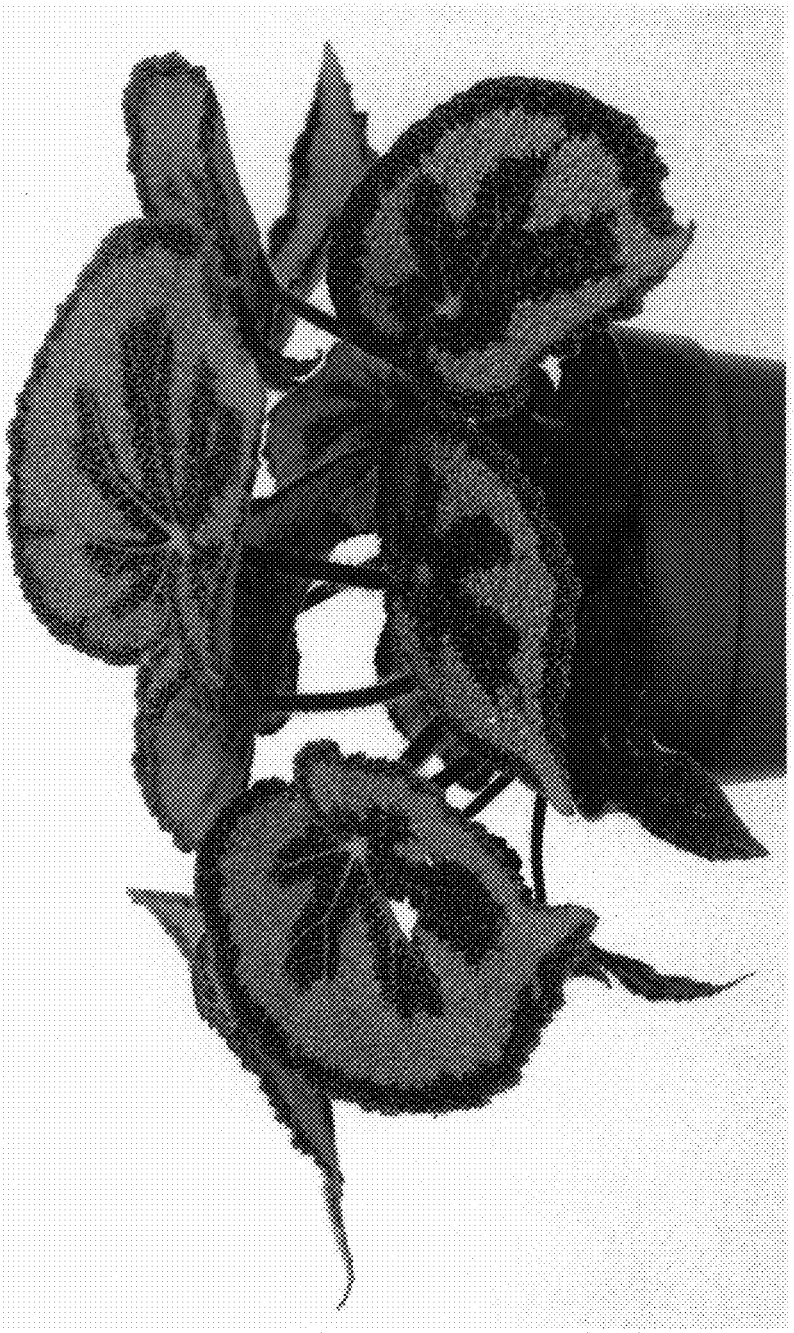

Latin name of the genus and species: *Begonia masoniana.*
Variety denomination: 'EC-BEGO-1902'.

BACKGROUND OF THE INVENTION

The new cultivar is the product of a planned breeding program. The new variety originated as the result of a crossing performed during 2014 of two unnamed, unpatented *Begonia masoniana* seedlings. The selection of the new variety was made in 2017, by the inventor at a greenhouse located in Sappemeer, The Netherlands.

Asexual reproduction of the new cultivar 'EC-BEGO-1902' was first performed at a greenhouse in Sappemeer, The Netherlands by leaf cuttings during March 2017. 'EC-BEGO-1902' has since produced several generations by vegetative cuttings and has shown that the unique features of this cultivar are stable and reproduced true to type.

SUMMARY OF THE INVENTION

The cultivar 'EC-BEGO-1902' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-BEGO-1902'. These characteristics in combination distinguish 'EC-BEGO-1902' as a new and distinct *Begonia masoniana* cultivar:

1. Unique striking brown leaf rim, with a distinct brown palmate center patch along veins, and bright green leaves.
2. Distinct hairy/puckered leaf upper surface.
3. Large distinctive leaves with long, thick petioles.

PARENT COMPARISON

Plants of the new cultivar 'EC-BEGO-1902' are similar to plants of the seed parent variety in most horticultural characteristics. However, plants of the new cultivar 'EC-BEGO-1902' differ in the following:

1. The new variety has a slightly larger plant habit than the seed parent.
2. The new variety has a slightly longer leaf stem than the seed parent.

Plants of the new cultivar 'EC-BEGO-1902' are similar to plants of the pollen parent variety in most horticultural characteristics. However, plants of the new cultivar 'EC-BEGO-1902' differ in the following:

1. The new variety has a brown leaf rim, while the pollen parent does not.
2. The new variety has slightly longer leaf stems than the pollen parent.
3. The new variety has thicker leaf stems than the pollen parent.

COMMERCIAL COMPARISON

Plants of the new cultivar 'EC-BEGO-1902' are similar to plants of the unpatented commercial variety, *Begonia* 'Iron Cross', in most horticultural characteristics. However, plants of the new cultivar 'EC-BEGO-1902' differ in the following:

1. The new variety has a brown leaf rim, while this comparator does not.
2. The new variety has a much higher plant habit than this comparator.
3. The new variety has much larger leaves than this comparator.

Plants of the new cultivar 'EC-BEGO-1902' are similar to plants of the commercial variety, *Begonia maculata* '77KL Sunrise', U.S. Plant Pat. No. 12,808, in most horticultural characteristics. However, plants of the new cultivar 'EC-BEGO-1902' differ in the following:

1. The new variety has broad ovate leaves with a brown rim, while this comparator has elongated green leaves with a white oval dot.
2. Leaves of the new variety have a hairy, puckered upper surface, while this comparator's leaves are sparely hirsute without puckering.

Plants of the new cultivar 'EC-BEGO-1902' are similar to plants of the commercial variety, *Begonia masoniana* 'EC-BEGO-1901', filed concurrently, and having U.S. application Ser. No. 16/873,178 in most horticultural characteristics. However, plants of the new cultivar 'EC-BEGO-1902' differ in the following:

1. 'EC-BEGO-1902' has larger foliage than 'EC-BEGO-1901'.
2. 'EC-BEGO-1902' is a larger plant than 'EC-BEGO-1901'.

BRIEF DESCRIPTION OF THE PHOTOGRAPHS

The accompanying photograph in FIG. 1 illustrates in full color a typical plant of 'EC-BEGO-1902' grown in a greenhouse. The plant is approximately 30 weeks of age in a 25 cm pot.

Figure 2:
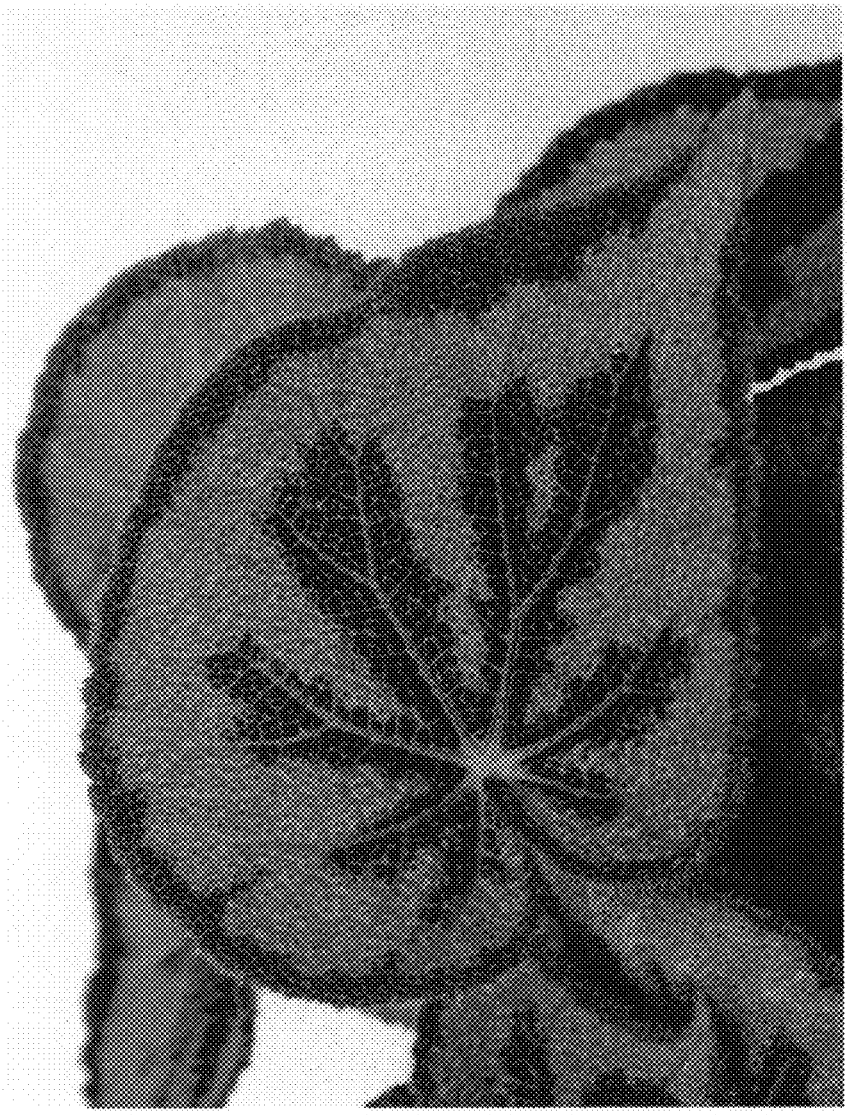

FIG. 2 illustrates a close up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 30-week-old 'EC-BEGO-1902' plants grown in September in a greenhouse in Sappemeer, The Netherlands. Measurements and numerical values represent averages of typical plant types.

Botanical classification: *Begonia masoniana* 'EC-BEGO-1902'.

Age of plant described: Approximately 30 weeks.

Container size: 14 cm.

Propagation:

Type of propagation typically used: Leaf cuttings.

Time to develop roots: About 15 days at approximately 21° C. in Summer.

Time to develop a rooted liner: About 70 days at approximately 21° C. in Summer.

Root description: Herbaceous, fine, moderately dense, freely branching. Brown in color, not accurately measured with R.H.S. chart.

Plant:

Plant type: Perennial potted plant.

Plant shape: Flattened globular.

Growth habit: Broad spreading upright.

Height: 18 cm.

Plant spread: 38.5 cm.

Growth rate: Moderate.

Plant vigor: Moderate to high.

Branching characteristics: No branches; leaves grow directly from base.

Foliage:

*Arrangement*.—Alternate, single, growing directly from roots.

*Average length*.—Approximately 16.7 cm.

*Average width*.—Approximately 11.6 cm.

*Shape of blade*.—Broad ovate.

*Apex*.—Long apiculate.

*Base*.—Oblique, lobes touching to slightly overlapping.

*Margin*.—Shallowly crenate, undulate, densely covered with short strigose hairs, average length 1.75 mm, colored RHS Greyed-Purple 185D.

*Texture of top surface*.—Strongly rugose and pubescent. Densely covered with short strigose hairs, average length 2.5 mm, colored RHS Greyed-Purple 185B.

*Texture of bottom surface*.—Pubescent. Densely covered with short strigose hairs, average length 1 mm, colored RHS Greyed-Purple 186D and lighter.

*Rugosity*.—Upper side: Strongly rugose. Under side: Slightly rugose.

*Luster*.—Upper side: Glossy. Under side: Matte.

*Color*.—Young foliage upper side: RHS Yellow-Green 144A, margined Yellow-Green 148A and slightly darker, area around main veins and secondary veins in the center of the leaf Brown 200C. Young foliage under side: RHS Yellow-Green N148A to N148B, narrowly margined Brown 200B. Mature foliage upper side: RHS Green 137B, margined in between Brown 200A to Black 203A, area around main veins and secondary veins in the center of the leaf Brown 200A to Black 203A. Mature foliage under side: RHS Yellow-Green N148B to 146C, margined Brown 200B to Greyed-Purple 183A, area around main veins and secondary veins in the center of the leaf between Greyed-Purple 183A and Brown 200B.

*Venation*.—Type: Laciniate. Venation color upper side: Considerably darker than RHS Yellow-Green N148A. Venation color under side: RHS Yellow-Green 148A.

*Petiole*.—Length: Approximately 12.5 cm. Diameter: Approximately 6 mm. Color: Upper side: RHS Brown N200A. Under side: RHS Grey-Brown N199A to Brown N200A. Texture: Densely pubescent with short hairs, average length 3.0 mm, colored RHS Greyed-Green 196D. Luster: Moderately glossy. Strength: Low.

Flower: Not observed to date.

Reproductive organs: Not observed to date.

Other characteristics:

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

Other features: Excellent weather tolerance.

What is claimed is:

1. A new and distinct cultivar of *Begonia* plant named 'EC-BEGO-1902' as herein illustrated and described.

* * * * *